US007893257B2

(12) United States Patent
Choudhury et al.

(10) Patent No.: US 7,893,257 B2
(45) Date of Patent: Feb. 22, 2011

(54) PROCESS FOR THE PREPARATION OF PIPERAZINYL AND DIAZEPANYL BENZAMIDE DERIVATIVES

(75) Inventors: Anusuya Choudhury, Churchville, PA (US); Jeffrey S. Grimm, Somerville, NJ (US); Kirk L. Sorgi, Doylestown, PA (US); David Palmer, Doylestown, PA (US); Jing Liu, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 426 days.

(21) Appl. No.: 11/953,262

(22) Filed: Dec. 10, 2007

(65) Prior Publication Data

US 2008/0171870 A1 Jul. 17, 2008

Related U.S. Application Data

(60) Provisional application No. 60/870,003, filed on Dec. 14, 2006.

(51) Int. Cl.
C07D 413/10 (2006.01)
(52) U.S. Cl. .................. 544/121; 544/106; 544/111
(58) Field of Classification Search ................ 544/106, 544/111, 114, 121
See application file for complete search history.

(56) References Cited

U.S. PATENT DOCUMENTS

| 2,525,223 | A | 10/1950 | Howard |
| 3,342,816 | A | 9/1967 | Mils et al. |
| 4,806,539 | A | 2/1989 | Petersen et al. |
| 2004/0110746 | A1 | 6/2004 | Apodaca et al. |
| 2005/0159431 | A1 | 7/2005 | Albrecht et al. |
| 2007/0066821 | A1 | 3/2007 | Allison et al. |

FOREIGN PATENT DOCUMENTS

| DE | 818805 C | 10/1951 |
| WO | WO 97/30992 | 8/1997 |
| WO | WO 02/20500 A2 | 3/2002 |
| WO | WO 02/062784 A1 | 8/2002 |
| WO | WO 2004/037801 A1 | 5/2004 |
| WO | WO 2006042103 A2 | 4/2006 |
| WO | WO 2006/067401 A1 | 6/2006 |

OTHER PUBLICATIONS

Bundgaard et al Design of Prodrugs Ed H. Bundgaard Elsevier 1985.
Greene et al Protective Groups in Organic Synthesis T.W. Green and P.G.M. Wuts 1991 Wiley & Sons.
Handbook of Pharmaceutical Excipients American Pharmaceutical Association and the Pharmaceutical Society of Great Britain 6th Ed.
McOmie et al Protective Groups in Organic Chemistry Eds J.F.W. McOmie Plenum Press 1973.
Pharmaceutical Dosage Forms: Tablets 2nd Ed Revised and Expanded vol. 1-3 Lieberman et al. Editor.
Pharmaceutical Dosage Forms: Parenteral Medications 2nd Ed vol. 1-2 Avis et al Editor.
Pharmaceutical Dosage Forms: Disperse Systems 2nd Ed vols. 1-2 Lieberman et al. Editor, Publisher Marcel Dekker Inc.
Barnes, J.C. et al.: The Selective Histamine H3 Receptor Antagonist thioperamide Improves Cognition and Enhances Hippocampal Acetylcholine Release in Vivo. Soc. Neurosci. Abstr. (1993) 19: 1813.
Chen, Z.: "Effect of histamine $H_3$-receptor antagonst clobenpropit on spatial memory of radial maze performance in rats"; Acta Pharmacol Sin (2000) 21(10): 905-910.
Fox, G.B. et al.: "Effects of histamine $H_3$ receptor ligands GT-2331 and ciproxifan in a repeated acquisition avoidance response in the spontaneously hypertensive rat pup"; Behavioural Brain Research (2002) 131: 151-161.
Lamberti, C. et al.: "Antidepressant-like effects of endogenous histamine and of two histamine $H_1$ receptor agonists in the mouse forced swim test"; British J. of Pharmacology (1998) 123(7): 1331-1336.
Leurs, R. et al.: The Medicinal Chemistry and Therapeutic Potentials of Ligands of the Histamine H3 Receptor; Prog. Drug. Res. (1995) 45: 107-165.
Machidori, H. et al.: Zucker Obese Rats: Defect in Brain Histamine Control of Feeding; Brain Res. (1992) 590: 180-186.
Miyazaki, S. et al.: "Effects of Thioperamide on the Cholinergic System and the Step-Through Passive Avoidance Test in Mice"; Meth Find Exp Clin Pharmacol (1995) 17(10): 653-658.
Miyazaki, S. et al.: "Effects of Thioperamide, a Histamine $H_3$-receptor Antagonist, on a Scopolamine-induced Learning Deficit Using an Elevated Plus-maze Test in Mice"; Life Sciences, (1995) 57(23): 2137-2144.
Orsetti, M. et al.: "Histamine $H_3$-receptor antagonism improves memory retention and reverses the cognitive deficit induced by scopolamine in a two-trial place recognition task"; Elsevier Behavioural Brain Research (2001) 124(2): 235-242.
Panula, P. et al.: Significant Changes in the Human Brain Histaminergic System in Alzheimer's Disease. Soc. Neurosci. Abstr. (1995) 21: 1977.
Perez-Garcia, C. et al.: "Effects of histamine $H_3$ receptor ligands in experimental models of anxiety and depression"; Psychopharmacology (1999) 142(2): 215-220.
Schlicker, E. et al.: The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353: 290-294.
Stark, H. et al.: Developments of Histamine H3-Receptor Antagonists. Drugs Future (1996) 21(5): 507-520.
Yokoyama, H. et al.: Effect of Thioperamide, a Histamine $H_3$ Receptor Antagonist, on Electrically Induced Convulsions in Mice. Eur. J. Pharmacol. (1993) 234: 129-133.
Partial International Search Report dated May 29, 2008 for International Appln No. PCT/US2007/086936.

*Primary Examiner*—Golam M Shameem
(74) *Attorney, Agent, or Firm*—Michael J. Atkins

(57) ABSTRACT

The present invention is directed to a novel process for the preparation of piperazinyl and diazepanyl benzamide derivatives, useful for the treatment of disorders and conditions mediated by a histamine receptor, preferably the H3 receptor.

2 Claims, No Drawings

PROCESS FOR THE PREPARATION OF PIPERAZINYL AND DIAZEPANYL BENZAMIDE DERIVATIVES

CROSS-REFERENCE TO RELATED APPLICATIONS

This application claims the benefit of U.S. Provisional Application 60/870,003, filed Dec. 14, 2006, which is hereby incorporated by reference in its entirety.

FIELD OF THE INVENTION

The present invention is directed to a novel process for the preparation of piperazinyl and diazepanyl benzamide derivatives, useful for the treatment of disorders and conditions mediated by a histamine receptor, preferably the H3 receptor.

BACKGROUND OF THE INVENTION

US Patent Application Publication 2004-0110746 A1, published Apr. 21, 2005 (also published as PCT Publication WO 04/037801, May 6, 2004), which is hereby incorporated by reference, discloses novel piperazinyl and diazepanyl benzamide derivatives useful for the treatment of histamine receptor mediated disorders. More specifically, the compounds are useful for the treatment of disorders and conditions mediated by the $H_3$ receptor. More particularly, the compounds are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, methods for preventing, inhibiting the progression of, or treating upper airway allergic response, asthma, itch, nasal congestion and allergic rhinitis.

US Patent Application Publication 2004-0110746 A1, published Apr. 21, 2005 (also published as PCT Publication WO 04/037801, May 6, 2004) discloses a process for the preparation of the piperazinyl and diazepanyl benzamides. There remains a need for processes for the preparation of piperazinyl and diazepanyl benzamide derivatives that are suitable for large scale/commercial applications.

SUMMARY OF THE INVENTION

The present invention is directed to a process for the preparation of a compound of formula (I)

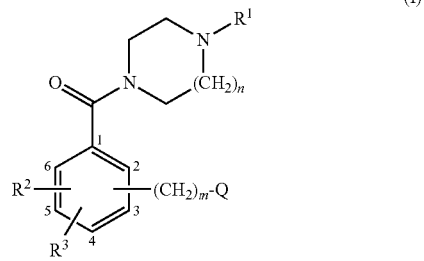

(I)

or a pharmaceutically acceptable salt, ester, tautomer, solvate or amide thereof;

wherein $R^1$ is selected from the group consisting of $C_{1-10}$alkyl (preferably, $C_{1-4}$alkyl), $C_{3-8}$ alkenyl, $C_{3-8}$cycloalkyl, $(C_{3-8}$cycloalkyl)$C_{1-6}$ alkyl, $(C_{3-8}$cycloalkyl)$C_{3-8}$alkenyl and $(C_{1-8}$alkylcarbonyl)$C_{1-8}$alkyl;

n is an integer from 1 to 2 (preferably, n is 1);

$R^2$ and $R^3$ are each independently selected from the group consisting of hydrogen, fluoro, chloro, bromo, nitro, trifluoromethyl, methyl and $C_{1-3}$alkoxy (preferably, $R^2$ and $R^3$ are each hydrogen);

m is an integer from 1 to 7; (preferably, m is an integer from 1 to 4, more preferably, m is 1);

Q is $NR^8R^9$;

wherein $R^8$ is selected from the group consisting of hydrogen, $C_{1-6}$alkyl, $C_{3-6}$alkenyl, 3-9 membered carbocyclyl, 3-12 membered heterocyclyl (preferably 5-9 or 5-8-membered heterocyclyl), phenyl, (6-9-membered heterocyclyl)$C_{1-6}$alkylene and (phenyl)$C_{1-6}$alkylene;

and $R^9$ is selected from the group consisting of $C_{1-6}$alkyl, $C_{3-6}$alkenyl, 6-9 membered carbocyclyl, 3-12 membered heterocyclyl (preferably 5-9 or 5-8-membered heterocyclyl), phenyl, (6-9-membered heterocyclyl)$C_{1-6}$alkylene, and (phenyl)$C_{1-6}$ alkylene;

alternatively, Q is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and N;

wherein Q (when Q is a saturated 3-12 membered N-linked heterocyclyl) is optionally substituted with 1-3 substituents independently selected from the group consisting of hydroxy, halo, carboxamide, $C_{1-6}$alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$alkylene, $C_{1-6}$alkoxy, $(C_{3-6}$cycloalkyl)-O—, phenyl, (phenyl)$C_{1-3}$alkylene, and (phenyl)$C_{1-3}$alkylene-O—;

where each of the above heterocyclyl, phenyl, and alkyl groups may be further optionally substituted with from 1 to 3 substituents independently selected from the group consisting of trifluoromethyl, methoxy, halo, nitro, cyano, hydroxy and $C_{1-3}$alkyl;

provided that the 5- and 6-positions on the phenyl ring are unsubstituted (i.e., the $R^2$, $R^3$ and —(CH$_2$)$_m$-Q are bound to the 2-, 3- and 4-positions on the phenyl ring);

provided further that when $R^1$ is methyl, then —(CH$_2$)$_m$-Q is not piperidin-1-ylmethyl;

and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;

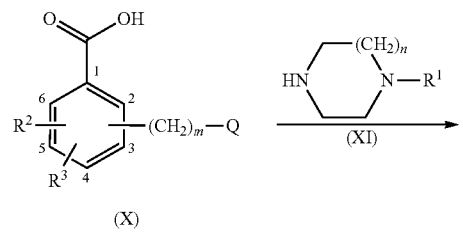

(X)

-continued

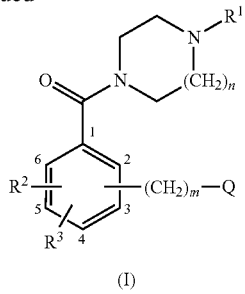

(I)

reacting a compound of formula (X) with a compound of formula (XI); in the presence of a peptide coupling agent; in an organic solvent or mixture thereof; to yield the corresponding compound of formula (I).

The present invention is further directed to a process for the preparation of a compound of formula (I)

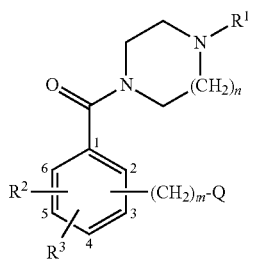

(I)

or a pharmaceutically acceptable salt, ester, tautomer, solvate or amide thereof;
wherein
$R^1$ is selected from the group consisting of $C_{1-10}$alkyl (preferably, $C_{1-4}$alkyl), $C_{3-8}$ alkenyl, $C_{3-8}$cycloalkyl, ($C_{3-8}$ cycloalkyl)$C_{1-6}$ alkyl, ($C_{3-8}$cycloalkyl)$C_{3-8}$alkenyl and ($C_{1-8}$ alkylcarbonyl)$C_{1-8}$alkyl;
n is an integer from 1 to 2 (preferably, n is 1);
$R^2$ and $R^3$ are each independently selected from the group consisting of hydrogen, fluoro, chloro, bromo, nitro, trifluoromethyl, methyl and $C_{1-3}$alkoxy (preferably, $R^2$ and $R^3$ are each hydrogen);
m is an integer from 1 to 7; (preferably, m is an integer from 1 to 4, more preferably, m is 1);
Q is $NR^8R^9$;
wherein $R^8$ is selected from the group consisting of hydrogen, $C_{1-6}$alkyl, $C_{3-6}$alkenyl, 3-9 membered carbocyclyl, 3-12 membered heterocyclyl (preferably 5-9 or 5-8-membered heterocyclyl), phenyl, (6-9-membered heterocyclyl)$C_{1-6}$alkylene and (phenyl)$C_{1-6}$alkylene;
and $R^9$ is selected from the group consisting of $C_{1-6}$alkyl, $C_{3-6}$alkenyl, 6-9 membered carbocyclyl, 3-12 membered heterocyclyl (preferably 5-9 or 5-8-membered heterocyclyl), phenyl, (6-9-membered heterocyclyl)$C_{1-6}$alkylene, and (phenyl)$C_{1-6}$ alkylene;
alternatively, Q is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and N;
wherein Q (when Q is a saturated 3-12 membered N-linked heterocyclyl) is optionally substituted with 1-3 substituents independently selected from the group consisting of hydroxy, halo, carboxamide, $C_{1-6}$alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$alkylene, $C_{1-6}$alkoxy, ($C_{3-6}$cycloalkyl)-O—, phenyl, (phenyl)$C_{1-3}$ alkylene, and (phenyl)$C_{1-3}$alkylene-O—;
where each of the above heterocyclyl, phenyl, and alkyl groups may be further optionally substituted with from 1 to 3 substituents independently selected from the group consisting of trifluoromethyl, methoxy, halo, nitro, cyano, hydroxy and $C_{1-3}$alkyl;
provided that the 5- and 6-positions on the phenyl ring are unsubstituted (i.e., the $R^2$, $R^3$ and —$(CH_2)_m$-Q are bound to the 2-, 3- and 4-positions on the phenyl ring);
provided further that when $R^1$ is methyl, then —$(CH_2)_m$-Q is not piperidin-1-ylmethyl;
and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;
comprising

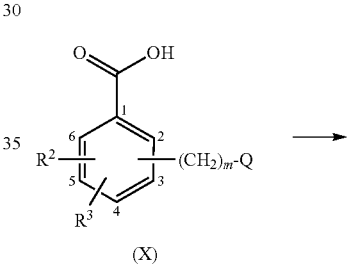

(X)

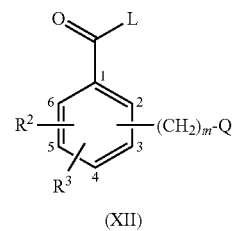

(XII)

activating a compound of formula (X), to yield the corresponding compound of formula (XII), wherein L is a leaving group;

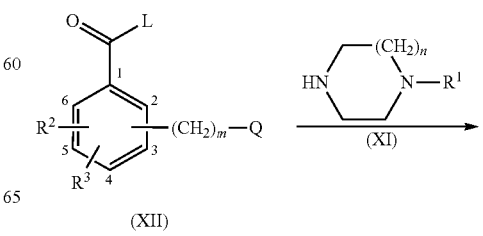

(XII)

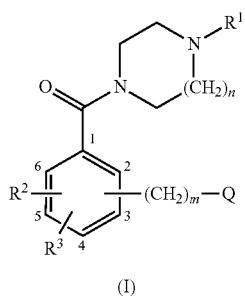

(I)

reacting the compound of formula (XII) with a compound of formula (XI); in the presence of a tertiary organic or inorganic base; in a solvent or mixture of solvents; to yield the corresponding compound of formula (I).

In an embodiment, the present invention is directed to processes for the preparation of a compound of formula (Ia)

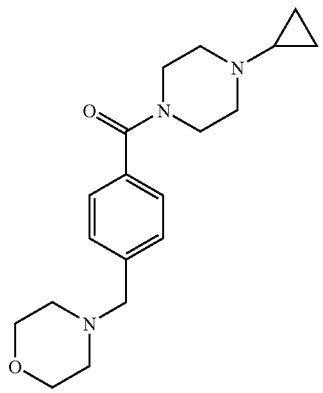

(Ia)

also known as (4-cyclopropyl-piperazin-1-yl)-(4-morpholin-4-ylmethyl-phenyl)-methanone, or its pharmaceutically acceptable salt thereof, preferably the corresponding di-hydrochloride salt.

In another embodiment, the present invention is directed to processes for the preparation of a compound of formula (Ib)

(Ib)

also known as (4-isopropyl-piperazin-1-yl)-(4-morpholin-4-ylmethyl-phenyl)-methanone, or its pharmaceutically acceptable salt thereof, preferably the corresponding monosuccinate salt.

The present invention is further directed to a process for the preparation of the compound of formula (XI)

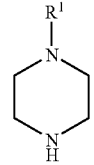

(XI)

wherein $R^1$ is selected from the group consisting of $C_{1-10}$alkyl (preferably, $C_{1-4}$alkyl), $C_{3-8}$ alkenyl, $C_{3-8}$cycloalkyl, ($C_{3-8}$ cycloalkyl)$C_{1-6}$ alkyl, ($C_{3-8}$cycloalkyl)$C_{3-8}$alkenyl and ($C_{1-8}$ alkylcarbonyl)$C_{1-8}$alkyl;

and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;

comprising reacting a compound of formula (XX), wherein X is hydrogen or a nitrogen protecting group and Z is a leaving group, with a compound of formula (XXI); in an organic solvent; to yield the corresponding compound of formula (XI).

In an embodiment, the present invention is further directed to a process for the preparation of the compound of formula (XIa)

(XIa)

also known as 1-cyclopropyl-piperazine. The compound of formula (XIa) is useful as a intermediate in the synthesis of compounds of formula (I) and more particularly, in the synthesis of the compound of formula (Ia).

In another embodiment, the present invention is further directed to a process for the preparation of the compound of formula (XIb)

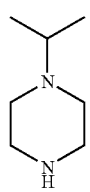

(XIb)

also known as 1-isopropyl-piperazine. The compound of formula (XIb) is useful as a intermediate in the synthesis of compounds of formula (I) and more particularly, in the synthesis of the compound of formula (Ib).

The present invention is further directed to a product prepared according to any of the processed described herein.

Illustrative of the invention is a pharmaceutical composition comprising a pharmaceutically acceptable carrier and a product prepared according to any of the processes described herein. An illustration of the invention is a pharmaceutical composition made by mixing a product prepared according to any of the processes described herein and a pharmaceutically acceptable carrier. Illustrating the invention is a process for making a pharmaceutical composition comprising mixing a product prepared according to any of the processes described herein and a pharmaceutically acceptable carrier.

Exemplifying the invention are methods of treating a disorder mediated by histamine, preferably, the $H_3$ histamine receptor, (selected from the group consisting of neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis) comprising administering to a subject in need thereof, a therapeutically effective amount of a products prepared according to any of the processes described herein or a pharmaceutical composition as described above.

Another example of the invention is the use of a product prepared according to any of the processes described herein in the preparation of a medicament for treating: (a) a sleep/wake disorder, (b) an arousal/vigilance disorders, (c) insomnia, (d) jet lag, (e) attention deficit hyperactivity disorders (ADHD), (f) a learning disorder, (g) a memory disorder, (h) cognitive dysfunction, (i) migraine, (j) neurogenic inflammation, (k) dementia, (l) mild cognitive impairment (pre-dementia), (m) Alzheimer's disease, (n) epilepsy, (o) narcolepsy, (p) an eating disorder, (q) obesity, (r) motion sickness, (s) vertigo, (t) schizophrenia, (u) substance abuse, (v) bipolar disorder, (w) manic disorder, (x) depression, (y) upper airway allergic response, (z) asthma, (aa) itch, (bb) nasal congestion or (cc) allergic rhinitis, in a subject in need thereof.

DETAILED DESCRIPTION OF THE INVENTION

The present invention is directed to processes for the preparation of compounds of formula (I)

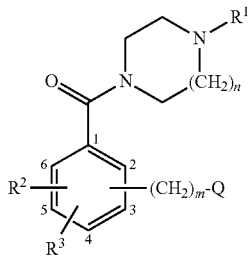

(I)

and pharmaceutically acceptable salts, esters, tautomers, solvates or amides thereof; wherein $R^1$, $R^2$, $R^3$, n, m and Q are as herein defined. The compounds formula (I) of the present invention are useful for the treatment of disorders and conditions mediated by a histamine receptor, preferably the H3 receptor.

Particularly, the compounds may be used in methods for treating or preventing neurologic or neuropsychiatric disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other disorders in which the histamine $H_3$ receptor is involved, such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis. Excessive daytime sleepiness (EDS) may occur with or without associated sleep apnea, shift work, fibromyalgia, MS, and the like.

The compounds of the present invention may be used in methods for treating or preventing disease states selected from the group consisting of: cognitive disorders, sleep disorders, psychiatric disorders, and other disorders.

Cognitive disorders include, for example, dementia, Alzheimer's disease (Panula, P. et al., Soc. Neurosci. Abstr. 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., Soc. Neurosci. Abstr. 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, REM-behavioral disorder, and jet lag. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., Naunyn-Schmiedeberg's Arch. Pharmacol. 1996, 353, 290-294), bipolar disorders, manic disorders, depression (Lamberti, C. et al. *Br. J. Pharmacol.* 1998, 123(7), 1331-1336; Perez-Garcia, C. et al. *Psychopharmacology* 1999, 142(2), 215-220) (Also see: Stark, H. et al., Drugs Future 1996, 21(5), 507-520; and Leurs, R. et al., Prog. Drug Res. 1995, 45, 107-165 and references cited therein.), obsessive-compulsive disorder, and post-traumatic stress disorder.

Other disorders include, for example, motion sickness, vertigo (including vertigo and benign postural vertigo), tinitus, epilepsy (Yokoyama, H. et al., Eur. J. Pharmacol. 1993, 234, 129-133), migraine, neurogenic inflammation, eating disorders (Machidori, H. et al., Brain Res. 1992, 590, 180-186), obesity, substance abuse disorders, movement disorders (e.g. restless leg syndrome), and eye-related disorders (e.g. macular degeneration and retinitis pigmentosis).

The present invention is further directed to processes for the preparation of compounds of formula (XI)

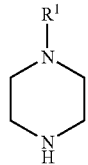

(XI)

wherein $R^1$ is as herein defined. The compounds of formula (XI) are useful as intermediates in the preparation of the compounds of formula (I).

As used herein, "$C_{a-b}$" (where a and b are integers) refers to a radical containing from a to b carbon atoms inclusive. For example, $C_{1-3}$ denotes a radical containing 1, 2 or 3 carbon atoms.

As used herein, "halo" or "halogen" shall mean monovalent radicals of chlorine, bromine, fluorine and iodine.

As used herein, the term "alkyl", whether used alone or as part of a substituent group, shall include straight and branched saturated carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a bivalent hydrocarbyl group, such as methylene (—$CH_2$—), ethylene (—$CH_2$—$CH_2$—) or propylene (—$CH_2CH_2CH_2$—), and so on.

As used herein, the term "alkylene" refers to a divalent straight- or branched-chain alkyl group. Suitable examples include, but are not limited to methylene, ethylene, n-propylene, and the like.

As used herein, unless otherwise noted, "alkenyl" shall mean an alkylene group with at least two hydrogen atoms replaced with a pi bond to form a carbon-carbon double bond, such as propenyl, butenyl, pentenyl, and so on. Where the alkenyl group is $R^8$ or $R^9$, the open radical (point of attachment to the rest of the molecule) is on $sp^3$ carbon, as illustrated by allyl, and the double bond or bonds is therefore at least alpha (if not beta, gamma, etc.) to the open radical.

As used herein, "alkylidene" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom on the rest of the molecule. Typical alkylidene radicals include, but are not limited to, ethanylidene; propylidenes such as propan-1-ylidene, propan-2-ylidene, cyclopropan-1-ylidene; butylidenes such as butan-1-ylidene, butan-2-ylidene, 2-methyl-propan-1-ylidene, cyclobutan-1-ylidene; and the like.

As used herein, unless otherwise noted, "alkoxy" shall denote an oxygen ether radical of the above-described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—$C_6H_4$—) which is preferably phen-1,4-diyl, but may also be phen-1,3-diyl.

As used herein, unless otherwise noted, "aralkyl" shall mean any alkyl group substituted with an aryl group such as phenyl, naphthyl, and the like. Examples of aralkyls include benzyl, phenethyl, and phenylpropyl.

As used herein, unless otherwise noted, "carbocyclyl" shall mean any cyclic group consisting of 3-12 carbon atoms, and preferably 6-9 carbon atoms, in the skeleton ring or rings, if the carbocycle is a fused or spiro bicyclic or tricyclic group. A carbocycle may be saturated, unsaturated, partially unsaturated, or aromatic. Examples include cycloalkyl, cycloalkenyl, cycloalkynyl; specific examples include phenyl, benzyl, indanyl, and biphenyl. A carbocycle may have substituents that are not carbon or hydrogen, such as hydroxy, halo, halomethyl, and so on as provided elsewhere herein.

As used herein, unless otherwise noted, the terms "heterocycle", "heterocyclyl" and "heterocyclo" shall denote any three-, four-, five-, six-, seven-, or eight-membered monocyclic, nine- or ten-membered bicyclic, or thirteen- or fourteen-membered tricyclic ring structure containing at least one heteroatom moiety selected from the group consisting of NH, O, SO, $SO_2$, (C=O), and S, and preferably NH, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom that results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

For example, where Q is a saturated 3-12 membered N-linked heterocyclyl, Q necessarily contains at least one nitrogen, and the carbon atoms are $sp^3$ hybridized. Where Q is a fused bicyclic heterocyclyl, the carbon atoms of the ring linked to L is $sp^3$ hybridized, provided the adjacent ring (and the common carbon atoms) may be $sp^2$, such as an indanyl where one of the carbon atoms has been replaced with nitrogen.

In general, exemplary bicyclic heterocyclyls include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo{2,3-c}pyridinyl, furo{3,1-b}pyridinyl), or furo{2,3-b}pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

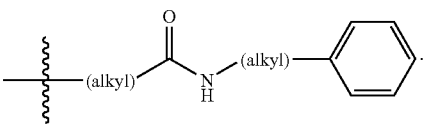

and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, thiomorpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl, tetrazolyl, oxadiazolyl,

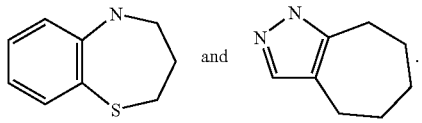

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl(alkyl)amido(alkyl)" substituent refers to a group of the formula

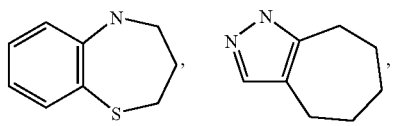

Unless otherwise noted, the position on the core phenyl ring of the compounds of formula (I) to which the $R^2$, $R^3$ and —$(CH_2)_m$-Q substituent groups are bound shall be defined as numbered in a clockwise direction around the phenyl ring, beginning with the carbon atom to which the —C(O)— group is bound, as drawn below

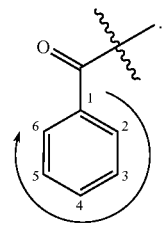

In the compounds of formula (I) of the present invention, $R^2$, $R^3$ and —$(CH_2)_m$-Q may be bound at the 2-, 3- and/or 4-positions only. Further, the 5- and 6-positions are unsubstituted. Thus, in the compounds of formula (I), the positions to which $R^2$, $R^3$ and —$(CH_2)_m$-Q are bound may be as listed below:

| 2-position | 3-position | 4-position |
|---|---|---|
| $R^2$ | $R^3$ | —$(CH_2)_m$-Q |
| $R^3$ | $R^2$ | —$(CH_2)_m$-Q |
| $R^2$ | —$(CH_2)_m$-Q | $R^3$ |
| $R^3$ | —$(CH_2)_m$-Q | $R^2$ |
| —$(CH_2)_m$-Q | $R^2$ | $R^3$ |
| —$(CH_2)_m$-Q | $R^3$ | $R^2$ |

Abbreviations used in the specification, particularly in the Schemes and Examples, are as follows:
BOC=t-Butoxycarbonyl
Cbz=Benzyloxycarbonyl
CDI=1,1-carbonyldiimidazole
DCC=N,N'-Dicyclohexyl-carbodiimide
DIPEA=Diisopropyl ethyl amine
DMF=Dimethylformamide
ECF=Ethylchloroformate
EDAC=1-(3-Dimethylaminopropyl)-3-ethylcarbodiimide hydrochloride
HATU=O-(7-Azabenzotriazol-1-yl)-N,N,N",N"'-Tetramethyluronium Hexafluorophosphate
HBTU=O-(1H-Benzotriazol-1-yl)-N,N,N',N'-tetramethyluronium hexafluorophosphate
HOBt=1-Hydroxybenzotriazole
HPLC=High Performance Liquid Chromatography
IBCF=Isobutylchloroformate
IPA=Isopropyl Alcohol
$NaBH(OAc)_3$=Sodium triacetoxyborohydride
NMR=Nuclear Magnetic Resonance
OBt=—O-(1-benzotriazolyl)
OMs=—O-mesyl (—O—$SO_2$—$CH_3$)
OTf=—O-triflyl (—O—$SO_2$—$CF_3$)
OTs=—O-tosyl (O—$SO_2$-(4-methylphenyl))
TBTU=O-(1H-Benzotriazol-1-yl)-N,N,N',N'-tetramethyluronium tertafluoroborate
TEA or $Et_3N$=Triethylamine
THF=Tetrahydrofuran The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, imidazolyl, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumeric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In an embodiment, the present invention is directed to processes for the preparation of compounds of formula (I) wherein $R^1$ is selected from the group consisting of $C_{1-6}$alkyl (preferably isopropyl) and $C_{3-8}$cycloalkyl (preferably cyclopropyl or cyclobutyl); n is 1; $R^2$ and $R^3$ are each hydrogen; $R^4$ is —(CH$_2$)-Q; and Q is a 5- to 6-membered N-linked heterocyclyl, wherein in addition to N-linking nitrogen, the heterocyclyl may optionally contain between 1 and 2 additional heteroatoms independently selected form O, S and NH.

In an embodiment, the present invention is directed to processes for the preparation of compounds of formula (I) wherein:
 (a) n is 1;
 (b) $R^1$ is $C_{1-10}$ alkyl (preferably branched);
 (c) $R^1$ is branched $C_{3-5}$ alkyl;
 (d) one of $R^2$, $R^3$ and $R^4$ is G; (preferably one of $R^3$ and $R^4$ is G)
 (e) $R^4$ is G;
 (f) L is unbranched —(CH$_2$)$_m$—, wherein m is an integer from 1 to 4;
 (g) L is —CH$_2$—;
 (h) Q is a saturated N-linked nitrogen-containing heterocyclyl;
 (i) Q is substituted or unsubstituted piperidinyl, diazepanyl, azepanyl, decahydroisoquinolin-2-yl, piperazinyl, pyrrolinyl, pyrrolidinyl, thiomorpholinyl, or morpholinyl;
 (j) Q is unsubstituted diazepanyl, azepanyl, morpholinyl, decahydroisoquinolin-2-yl, piperidinyl, or pyrrolidinyl;
 (k) substituted Q are selected from N—($C_{1-6}$ alkyl)piperazinyl, N-phenyl-piperazinyl, 1,3,8-triaza-spiro{4.5}decyl, and 1,4-dioxa-8-aza-spiro{4.5}decyl;
 (l) Q is a monovalent radical of an amine selected from aziridine, 1,4,7-trioxa-10-aza-cyclododecane, thiazolidine, 1-phenyl-1,3,8-triaza-spiro{4.5}decan-4-one, piperidine-3-carboxylic acid diethylamide, 1,2,3,4,5,6-hexahydro-{2,3'}bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, {2-(3,4-dimethoxy-phenyl)-ethyl}-methyl-amine, thiomorpholinyl, allyl-cyclopentyl-amine, {2-(1H-indol-3-yl)-ethyl}-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, and pyridin-2-ylamine;

(m) Q is selected from diazepanyl, azepanyl, morpholinyl, piperidinyl, and pyrrolidinyl, optionally substituted with between 1 and 3 substituents independently selected from hydroxy, halo, carboxamide, $C_{1-6}$ alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$ alkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O—, where each of above heterocyclyl, phenyl, and alkyl groups may be optionally substituted with from 1 to 3 substituents independently selected from trifluoromethyl, methoxy, halo, nitro, cyano, hydroxy, and $C_{1-3}$ alkyl;

(n) Q is substituted with a substituent comprising a 5-9 membered or 6-9 membered heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, pyrrolidinyl, and pyrrolyl;

(o) Q is piperidinyl;
(p) $R^8$ is hydrogen;
(q) $R^9$ is $C_{1-6}$ alkyl;
(r) $R^9$ is unsubstituted or substituted phenyl;
(s) $R^8$ and $R^9$ independently are $C_{1-6}$ alkyl;
(t) $R^8$ and $R^9$ are methyl;
(u) $R^8$ and $R^9$ are ethyl;
(v) $R^9$ is selected from phenyl or 5-9 membered aromatic heterocyclyl, wherein said phenyl or aromatic heterocyclyl is optionally substituted with 1-3 substituents selected from methoxy, hydroxy, halo, nitro, cyano, trifluoromethyl, and $C_{1-3}$ alkyl;

(w) $R^9$ is selected from substituted or unsubstituted phenyl, pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, pyrrolidinyl, and pyrrolyl;

(x) $R^9$ is substituted or unsubstituted pyridyl;
(y) X is O; and
(z) combinations of (a) through (z) above.

In another embodiment, the present invention is directed to processes for the preparation of compounds of formula (I) selected from the group consisting of:

(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-ylmethyl-phenyl)-{4-(1-ethyl-propyl)-piperazin-1-yl}-methanone;
(4-Butyl-piperazin-1-yl)-(4-dimethylaminomethyl-phenyl)-methanone;
(4-Butyl-piperazin-1-yl)-(4-morpholin-4-ylmethyl-phenyl)-methanone;
(4-Butyl-piperazin-1-yl)-{4-(3-trifluoromethyl-piperidin-1-ylmethyl)-phenyl}-methanone;
(4-Butyl-piperazin-1-yl)-{4-{(4-trifluoromethyl-phenylamino)-methyl}-phenyl}-methanone;
(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(3-morpholin-4-ylmethyl-phenyl)-methanone;
(4-Isopropyl-piperazin-1-yl)-(3-piperidin-1-ylmethyl-phenyl)-methanone;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-phenylaminomethyl-phenyl)-methanone dihydrochloride;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-(4-isopropyl-piperazin-1-ylmethyl)-phenyl}-methanone;
(4-Isopropyl-piperazin-1-yl)-{4-[(2-methoxy-ethylamino)-methyl]-phenyl}-methanone;
(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-Isopropyl-piperazin-1-yl)-{4-{(4-trifluoromethyl-phenylamino)-methyl}-phenyl}-methanone;
(4-Isopropyl-piperazin-1-yl)-{4-{(4-trifluoromethyl-pyridin-2-ylamino)-methyl}-phenyl}-methanone dihydrochloride;
(4-Isopropyl-piperazin-1-yl)-{4-{(5-trifluoromethyl-pyridin-2-ylamino)-methyl}-phenyl}-methanone dihydrochloride;
(4-Isopropyl-piperazin-1-yl)-{4-{(6-trifluoromethyl-pyridin-3-ylamino)-methyl}-phenyl}-methanone dihydrochloride;
(4-Methyl-piperazin-1-yl)-(4-morpholin-4-ylmethyl-phenyl)-methanone dihydrochloride;
(4-Methyl-piperazin-1-yl)-(4-piperidin-1-ylmethyl-phenyl)-methanone dihydrochloride;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-phenylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
(4-sec-Butyl-piperazin-1-yl)-{4-(3-trifluoromethyl-piperidin-1-ylmethyl)-phenyl}-methanone dihydrochloride;
{3-(4-Benzyl-piperidin-1-ylmethyl)-phenyl}-(4-methyl-piperazin-1-yl)-methanone;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-phenylaminomethyl-phenyl)-methanone dihydrochloride;

{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-ylmethyl)-phenyl}-methanone dihydrochloride;
{4-(1-Ethyl-propyl)-piperazin-1-yl}-{4-(decahydro-isoquinolin-2-ylmethyl)-phenyl}-methanone;
{4-(1-Ethyl-propyl)-piperazin-1-yl}-{4-{(4-trifluoromethyl-phenylamino)-methyl}-phenyl}-methanone dihydrochloride;
{4-(1-Methyl-heptyl)-piperazin-1-yl}-(4-morpholin-4-ylmethyl-phenyl)-methanone;
{4-(1-Methyl-heptyl)-piperazin-1-yl}-(4-piperidin-1-ylmethyl-phenyl)-methanone;
{4-(Benzylamino-methyl)-phenyl}-(4-isopropyl-piperazin-1-yl)-methanone dihydrochloride;
{4-(Benzylamino-methyl)-phenyl}-{4-(1-ethyl-propyl)-piperazin-1-yl}-methanone;
{4-{(5-Chloro-pyridin-2-ylamino)-methyl}-phenyl}-(4-isopropyl-piperazin-1-yl)-methanone dihydrochloride;
(4-Cyclopropyl-piperazin-1-yl)-(4-morpholin-4-ylmethyl-phenyl)-methanone;
(4-Cyclopropyl-piperazin-1-yl)-(4-morpholin-4-ylmethyl-phenyl)-methanone dihydrochloride; and
(4-Cyclobutyl-piperazin-1-yl)-(4-morpholin-4-ylmethyl-phenyl)-methanone.

Preferably, the processes of the present invention are directed to making compounds selected from the group consisting of:
(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-ylmethyl-phenyl)-{4-(1-ethyl-propyl)-piperazin-1-yl}-methanone;
(4-Butyl-piperazin-1-yl)-(4-dimethylaminomethyl-phenyl)-methanone;
(4-Butyl-piperazin-1-yl)-(4-morpholin-4-ylmethyl-phenyl)-methanone;
(4-Butyl-piperazin-1-yl)-{4-(3-trifluoromethyl-piperidin-1-ylmethyl)-phenyl}-methanone;
(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(3-piperidin-1-ylmethyl-phenyl)-methanone;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-phenylaminomethyl-phenyl)-methanone dihydrochloride;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-(4-isopropyl-piperazin-1-ylmethyl)-phenyl}-methanone;
(4-Isopropyl-piperazin-1-yl)-{4-[(2-methoxy-ethylamino)-methyl]-phenyl}-methanone;
(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-Isopropyl-piperazin-1-yl)-{4-{(5-trifluoromethyl-pyridin-2-ylamino)-methyl}-phenyl}-methanone dihydrochloride;
(4-Isopropyl-piperazin-1-yl)-{4-{(6-trifluoromethyl-pyridin-3-ylamino)-methyl}-phenyl}-methanone dihydrochloride;
(4-Methyl-piperazin-1-yl)-(4-morpholin-4-ylmethyl-phenyl)-methanone dihydrochloride;
(4-Methyl-piperazin-1-yl)-(4-piperidin-1-ylmethyl-phenyl)-methanone dihydrochloride;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-phenylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
(4-sec-Butyl-piperazin-1-yl)-{4-(3-trifluoromethyl-piperidin-1-ylmethyl)-phenyl}-methanone dihydrochloride;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-ylmethyl)-phenyl}-methanone dihydrochloride;
{4-(1-Ethyl-propyl)-piperazin-1-yl}-{4-(decahydro-isoquinolin-2-ylmethyl)-phenyl}-methanone;
{4-(Benzylamino-methyl)-phenyl}-(4-isopropyl-piperazin-1-yl)-methanone dihydrochloride;
{4-(Benzylamino-methyl)-phenyl}-{4-(1-ethyl-propyl)-piperazin-1-yl}-methanone;
{4-{(5-Chloro-pyridin-2-ylamino)-methyl}-phenyl}-(4-isopropyl-piperazin-1-yl)-methanone dihydrochloride;
(4-Cyclopropyl-piperazin-1-yl)-(4-morpholin-4-ylmethyl-phenyl)-methanone;
(4-Cyclopropyl-piperazin-1-yl)-(4-morpholin-4-ylmethyl-phenyl)-methanone dihydrochloride; and
(4-Cyclobutyl-piperazin-1-yl)-(4-morpholin-4-ylmethyl-phenyl)-methanone.

Preferably, the present invention is directed to processes for the preparation of a compound of formula (I) selected from the group consisting of:
(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-ylmethyl-phenyl)-{4-(1-ethyl-propyl)-piperazin-1-yl}-methanone;

(4-Butyl-piperazin-1-yl)-(4-morpholin-4-ylmethyl-phenyl)-methanone;
(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-[(2-methoxy-ethylamino)-methyl]-phenyl}-methanone;
(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-ylmethyl)-phenyl}-methanone dihydrochloride;
{4-(1-Ethyl-propyl)-piperazin-1-yl}-{4-(decahydro-isoquinolin-2-ylmethyl)-phenyl}-methanone;
{4-(Benzylamino-methyl)-phenyl}-(4-isopropyl-piperazin-1-yl)-methanone dihydrochloride;
{4-(Benzylamino-methyl)-phenyl}-{4-(1-ethyl-propyl)-piperazin-1-yl}-methanone;
(4-Cyclopropyl-piperazin-1-yl)-(4-morpholin-4-ylmethyl-phenyl)-methanone;
(4-Cyclopropyl-piperazin-1-yl)-(4-morpholin-4-ylmethyl-phenyl)-methanone dihydrochloride; and
(4-Cyclobutyl-piperazin-1-yl)-(4-morpholin-4-ylmethyl-phenyl)-methanone.

More preferably, the present invention is directed to processes for the preparation of a compound of formula (I) selected from the group consisting of:
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Cyclohexyl-piperazin-1-yl)-(4-piperidin-1-ylmethyl-phenyl)-methanone;
(4-Isopropyl-piperazin-1-yl)-(4-morpholin-4-ylmethyl-phenyl)-methanone;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-{4-(3-trifluoromethyl-piperidin-1-ylmethyl)-phenyl}-methanone dihydrochloride;
(4-sec-Butyl-piperazin-1-yl)-(4-dimethylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
(4-Cyclopropyl-piperazin-1-yl)-(4-morpholin-4-ylmethyl-phenyl)-methanone;
(4-Cyclopropyl-piperazin-1-yl)-(4-morpholin-4-ylmethyl-phenyl)-methanone dihydrochloride; and
(4-Cyclobutyl-piperazin-1-yl)-(4-morpholin-4-ylmethyl-phenyl)-methanone.

More preferably still, the present invention is directed to processes for the preparation of a compound of formula (I) selected from the group consisting of:
(4-Azepan-1-ylmethyl-phenyl)-(4-sec-butyl-piperazin-1-yl)-methanone;
(4-Isopropyl-piperazin-1-yl)-(4-piperidin-1-ylmethyl-phenyl)-methanone;
(4-Isopropyl-piperazin-1-yl)-(4-morpholin-4-ylmethyl-phenyl)-methanone;
(4-sec-Butyl-piperazin-1-yl)-(4-piperidin-1-ylmethyl-phenyl)-methanone;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
(4-sec-Butyl-piperazin-1-yl)-(4-morpholin-4-ylmethyl-phenyl)-methanone dihydrochloride;
{4-(1-Ethyl-propyl)-piperazin-1-yl}-(4-morpholin-4-ylmethyl-phenyl)-methanone dihydrochloride;
(4-Cyclopropyl-piperazin-1-yl)-(4-morpholin-4-ylmethyl-phenyl)-methanone;
(4-Cyclopropyl-piperazin-1-yl)-(4-morpholin-4-ylmethyl-phenyl)-methanone dihydrochloride; and
(4-Cyclobutyl-piperazin-1-yl)-(4-morpholin-4-ylmethyl-phenyl)-methanone.

In an embodiment, the present invention is directed to processes for the preparation of compounds of formula (I) or pharmaceutically acceptable salts thereof, wherein $R^1$ is cycloalkyl, preferably cycylopropyl. In another embodiment, the present invention is directed to processes for the preparation of compounds of formula (I) or pharmaceutically acceptable salts thereof, wherein $R^1$ is a branched alkyl, preferably isopropyl.

In an embodiment of the present invention, the present invention is directed to processes for the preparation of a compound selected from the group consisting of the compound of formula (Ia), the compound of formula (Ib) and pharmaceutically acceptable salts thereof. In another embodiment, the present invention is directed to processes for the preparation of the compound selected from the group consisting of the compound of formula (Ia), the di-hydrochloride salt of the compound of formula (Ia), the compound of formula (Ib) and the mono-succinate salt of the compound of formula (Ib).

The present invention is directed to a process for the preparation of compounds of (I) as outlined in Scheme 1, below.

dazolide, and the like, preferably chloro. For example, wherein the leaving group is chloro, the compound of formula (X) is activated by reacting with a suitably selected source of chlorine such as thionyl chloride, oxalyl chloride, and the like.

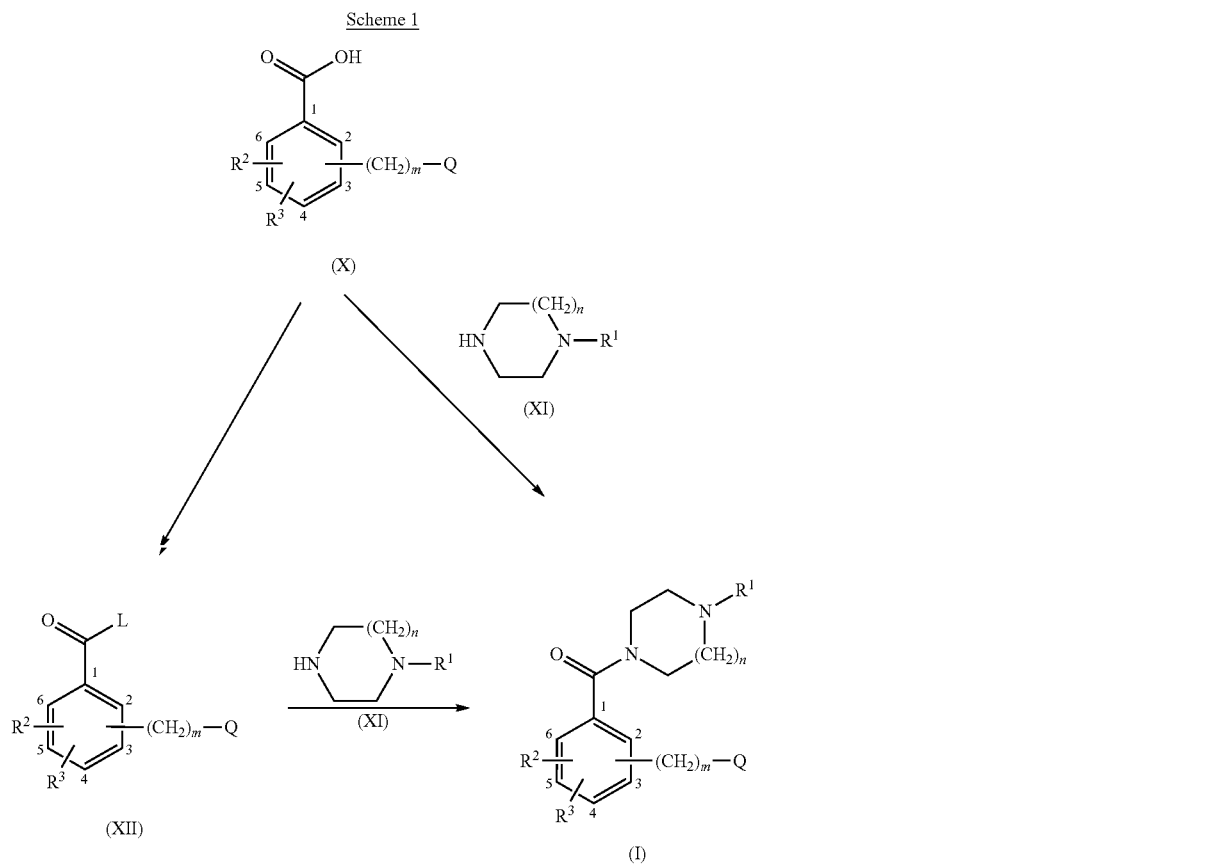

Accordingly, a suitably substituted compound of formula (X), a known compound or compound prepared by known methods, is reacted with a suitably substituted compound of formula (XI), a known compound or compound prepared by known methods; wherein the compound of formula (XI) is preferably present in an amount in the range of from about 0.95 to about 1.25 molar equivalents, or any range therein, more preferably about 1.1 molar equivalents;

in the presence of a suitably selected peptide coupling agent such as HOBt/EDAC, ECF, IBCF, CDI, HATU, HBTU, TBTU, DCC, and the like, preferably HOBt/EDAC; wherein the coupling agent is present in a amount in the range of from about a catalytic amount to about a 1 molar equivalent (relative to the molar amount of the compound of formula (X)), or any range therein, preferably, about 1 molar equivalent;

in an organic solvent or mixture thereof, such as toluene, acetonitrile, ethyl acetate, DMF, THF, methylene chloride, and the like, preferably a mixture of toluene and acetonitrile at a ratio of about 4:1 volume:volume;

to yield the corresponding compound of formula (I).

Alternatively, the compound of formula (X) is activated according to known methods, to yield the corresponding compound of formula (XII), wherein L is a suitable leaving group such as chloro, bromo, —OC(O)—O—$C_{1-4}$alkyl, imi- The compound of formula (XII) is reacted with a suitably substituted compound of formula (XI), a known compound or compound prepared by known methods; wherein the compound of formula (XI) is preferably present in an amount in the range of from about 1 to about 3 molar equivalents, or any range therein, preferably from about 1 to about 1.2 molar equivalents; in the presence of a suitably selected tertiary organic or inorganic base such as TEA, NaOH, $Na_2CO_3$, and the like, preferably an inorganic base, more preferably a 1:1 molar ratio mixture of NaOH and $Na_2CO_3$; wherein the tertiary organic or inorganic base is preferably present in an amount in the range of from about 4 to about 10 molar equivalents, or any range therein, more preferably, in an amount in the range of from about 4 to about 6 molar equivalents; in a solvent or mixture thereof, such as toluene, dichloromethane, THF, water, and the like, preferably a mixture of toluene and water, wherein the molar ratio of toluene to water is preferably in the range of from about 2:1 to about 1:2; to yield the corresponding compound of formula (I).

The compound of formula (I) may be optionally isolated according to known methods, for example by filtration, solvent evaporation, distillation, and the like. The compound of formula (I) may be further optionally purified according to known methods, for example by recrystallization, column chromatography, and the like.

Alternatively, the compound of formula (I) may be reacted with a suitably selected acid, to yield the corresponding acid addition salt, which salt may be isolated and/or purified according to known methods.

In an embodiment, the present invention is directed to a process for the preparation of the compound of formula (Ia), as described in more detail in Scheme 2 below.

the coupling agent is present in a amount in the range of from about a catalytic amount to about a 1 molar equivalent (relative to the molar amount of the compound of formula (X)), preferably, about 1 molar equivalent;

in an organic solvent or mixture thereof, such as toluene, acetonitrile, ethyl acetate, DMF, THF, methylene chloride, and the like, preferably a mixture of toluene and acetonitrile at a ratio of about 4:1 volume:volume;

to yield the corresponding compound of formula (Ia).

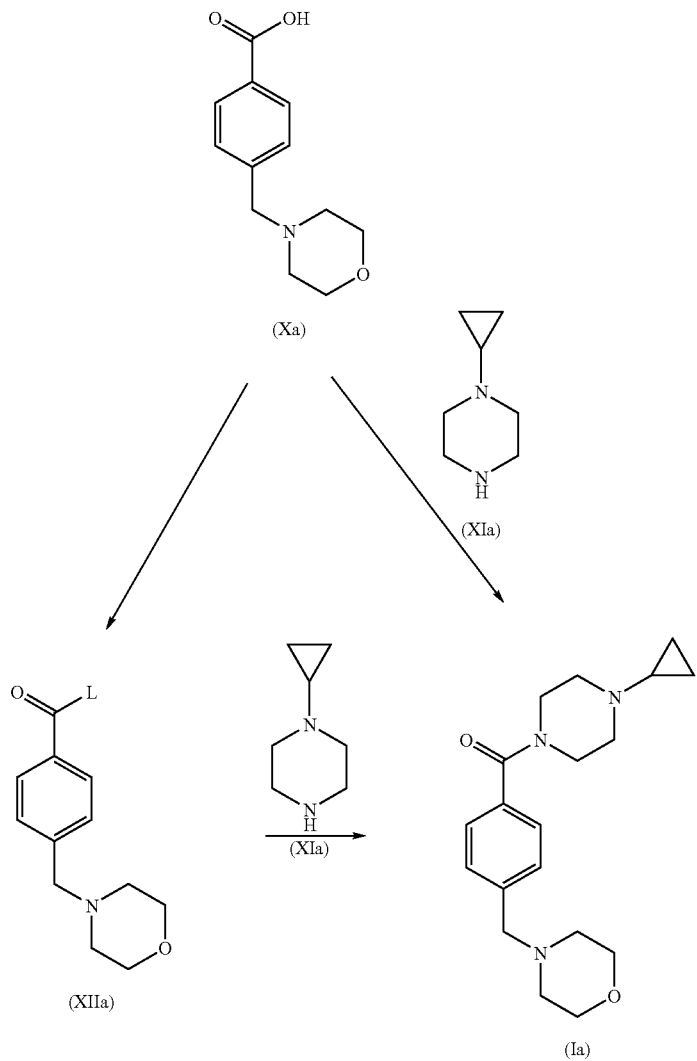

Scheme 2

Accordingly, a suitably substituted compound of formula (Xa), also known as 4-morpholin-4-ylmethyl-benzoic acid, a known compound, is reacted with a suitably substituted compound of formula (XIa), also known as 1-cyclopropyl-piperazine, a known compound; wherein the compound of formula (XIa) is preferably present in an amount in the range of from about 0.95 to about 1.25 molar equivalents, more preferably about 1.1 molar equivalents;

in the presence of a suitably selected peptide coupling agent such as HOBt/EDAC, ECF, IBCF, CDI, HATU, HBTU, TBTU, DCC, and the like. preferably HOBt/EDAC; wherein Alternatively, the compound of formula (Xa) is activated according to known methods, to yield the corresponding compound of formula (XIIa), wherein L is a suitable leaving group such as chloro, bromo, —OC(O)—O—$C_{1-4}$alkyl, imidazolide, and the like, preferably chloro. For example, wherein the leaving group is chloro, the compound of formula (Xa) is activated by reacting with a suitably selected source of chlorine such as thionyl chloride, oxalyl chloride, and the like.

The compound of formula (XIIa) is reacted with a suitably substituted compound of formula (XIa), a known compound or compound prepared by known methods; wherein the compound of formula (XIa) is preferably present in an amount in the range of from about 1 to about 3 molar equivalents, preferably from about 1 to about 1.2 molar equivalents; in the presence of a suitably selected tertiary organic or inorganic base such as TEA, NaOH, Na$_2$CO$_3$, and the like, preferably an inorganic base, more preferably a 1:1 molar ratio mixture of NaOH and Na$_2$CO$_3$; wherein the tertiary organic or inorganic base is preferably present in an amount in the range of from about 4 to about 10 molar equivalents, more preferably, in an amount in the range of from about 4 to about 6 molar equivalents; in a solvent or mixture thereof, such as toluene, dichloromethane, THF, water, and the like, preferably a mixture of toluene and water, wherein the molar ratio of toluene to water is preferably in the range of from about 2:1 to about 1:2; to yield the corresponding compound of formula (Ia).

The compound of formula (Ia) may be optionally isolated according to known methods, for example by filtration, solvent evaporation, distillation, and the like. The compound of formula (Ia) may be further optionally purified according to known methods, for example by recrystallization, column chromatography, and the like. Preferably, the compound of formula (Ia) is isolated by solvent evaporation and purified by salt formation as described below.

Alternatively, the compound of formula (Ia) is reacted with a suitably selected acid, to yield the corresponding acid addition salt. Preferably, the compound of formula (Ia) is reacted with HCl acid, in an organic solvent, preferably in an alcohol such as ethyl acetate, THF, dioxane, diethyl ethyl, IPA, ethanol, and the like, preferably, the compound of formula (Ia) is reacted with 5/6N HCl in IPA, to yield the corresponding acid addition salt. One skilled in the art will recognize that for the compound of formula (Ia) reacted with 5/6N HCl, the corresponding acid addition salt is a di-hydrochloride salt. More specifically, the process yields the crystalline, di-hydrochloride salt.

The crystalline di-hydrchloride salt of the compound of formula (Ia) is further optionally isolated and/or purified according to known methods, for example isolated by filtration, solvent evaporation, and the like and purified by recrystallization, column chromatography, and the like. Preferably, the di-hydrochloride salt of the compound of formula (Ia) is purified by recrystallized from a mixture of ethanol and water, at a ratio of 90 L:15 L.

In another embodiment, the present invention is directed to a process for the preparation of the compound of formula (Ib), as described in more detail in Scheme 3, below.

Scheme 3

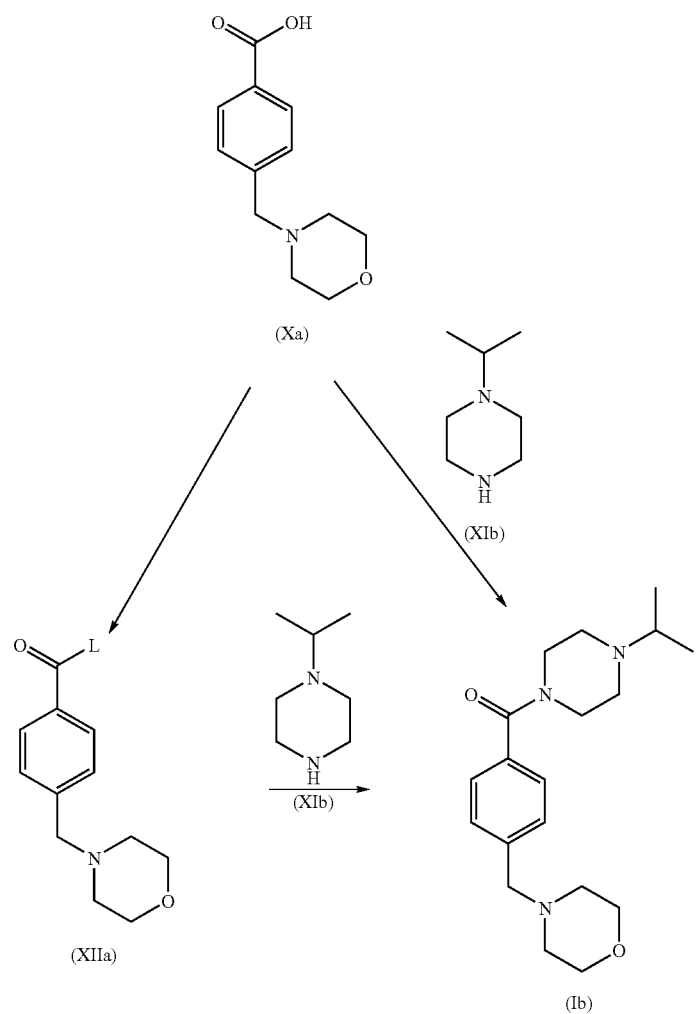

Accordingly, a suitably substituted compound of formula (Xb), also known as also known as 4-morpholin-4-ylmethyl-benzoic acid, a known compound, is reacted with a suitably substituted compound of formula (XIb), also known as 1-iso-propyl-piperazine, a known compound; wherein the compound of formula (XIa) is preferably present in an amount in the range of from about 0.95 to about 1.25 molar equivalents, more preferably about 1.1 molar equivalents;

in the presence of a suitably selected peptide coupling agent such as HOBt/EDAC, ECF, IBCF, CDI, HATU, HBTU, TBTU, DCC, and the like. preferably HOBt/EDAC; wherein the coupling agent is present in a amount in the range of from about a catalytic amount to about a 1 molar equivalent (relative to the molar amount of the compound of formula (X)), preferably, about 1 molar equivalent;

in an organic solvent or mixture thereof, such as toluene, acetonitrile, ethyl acetate, DMF, THF, methylene chloride, and the like, preferably a mixture of toluene and acetonitrile at a ratio of about 4:1 volume:volume;

to yield the corresponding compound of formula (Ib).

Alternatively, the compound of formula (Xb) is activated according to known methods, to yield the corresponding compound of formula (XII), wherein L is a suitable leaving group such as chloro, bromo, —OC(O)—O—$C_{1-4}$alkyl, imidazolide, and the like, preferably chloro. For example, wherein the leaving group is chloro, the compound of formula (Xb) is activated by reacting with a suitably selected source of chlorine such as thionyl chloride, oxalyl chloride, and the like.

The compound of formula (XIIb) is reacted with a suitably substituted compound of formula (XIb), a known compound or compound prepared by known methods; wherein the compound of formula (XIb) is preferably present in an amount in the range of from about 1 to about 3 molar equivalents, preferably from about 1 to about 1.2 molar equivalents; in the presence of a suitably selected tertiary organic or inorganic base such as TEA, NaOH, $Na_2CO_3$, and the like, preferably an inorganic base, more preferably a 1:1 molar ratio mixture of NaOH and $Na_2CO_3$; wherein the tertiary organic or inorganic base is preferably present in an amount in the range of from about 4 to about 10 molar equivalents, more preferably, in an amount in the range of from about 4 to about 6 molar equivalents; in a solvent or mixture thereof, such as toluene, dichloromethane, THF, water, and the like, preferably a mixture of toluene and water, wherein the molar ratio of toluene to water is preferably in the range of from about 2:1 to about 1:2; to yield the corresponding compound of formula (Ib).

The compound of formula (Ib) may be optionally isolated and/or purified according to known methods, for example by filtrations, solvent evaporation, distillation, column chromatography, recrystallization, and the like. Preferably, the compound of formula (Ib) is isolated by solvent evaporation and purified by salt formation as described herein.

Alternatively, the compound of formula (Ib) is reacted with a suitably selected acid, to yield the corresponding acid addition salt. Preferably, the compound of formula (Ib) is reacted with succinic acid, in an organic solvent such as THF, toluene, acetonitrile, and the like, preferably in an organic solvent in which succinic acid is soluble, more preferably in THF, to yield the corresponding mono-succinate addition salt.

The mono-succinate salt of the compound of formula (Ib) is further optionally isolated and/or purified according to known methods. Preferably, the mono-succinate salt of the compound of formula (Ib) is purified by recrystallization from a suitable solvent such as absolute ethanol, methanol, isopropyl alcohol, acetonitrile, and the like, preferably from absolute ethanol.

Compounds of formula (X) are known compounds or compounds which may be prepared according to known methods. As an example, Scheme 4 below outlines a process for the preparation of the compound of formula (Xa).

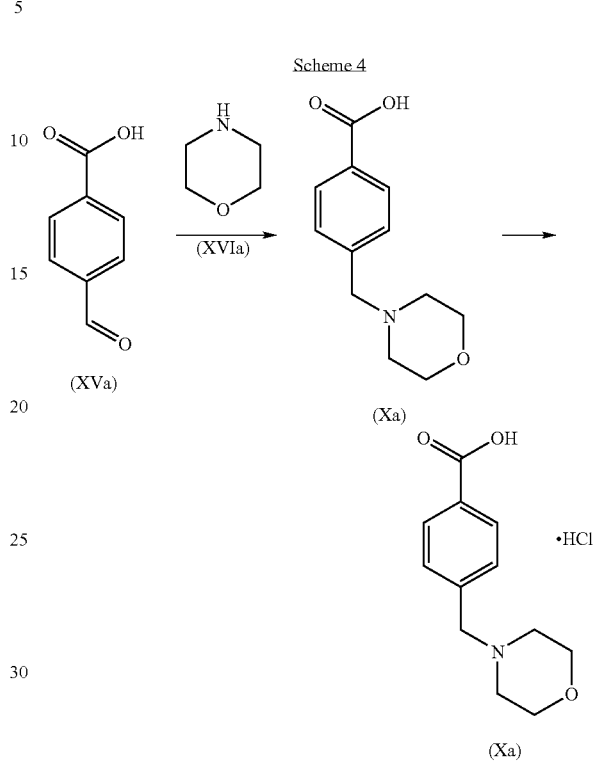

Scheme 4

Accordingly, a suitably substituted compound of formula (XVa), also known as 4-formyl-benzoic acid, a known compound or compound prepared by known methods, is reacted with a suitably substituted compound of formula (XVIa), also known as morpholine, a known compound; wherein the compound of formula (XVIa) is preferably present in an amount in the range of from about 1 to about 5 molar equivalents, or any range therein, more preferably, the compound of formula (XVIa) is present in an amount in the range of from about 1.5 to about 2.5 molar equivalents, more preferably still, the compound of formula (XVIa) is present in an amount in the range of from about 1.25 to about 1.5 molar equivalents; in the presence of a reducing agent such as $NaBH(OAc)_3$, $NaBH_4$, sodium cyanoborohydride, and the like, preferably, $NaBH(OAc)_3$; wherein the reducing agent is preferably present in an amount in the range of from about 1 to about 2 equivalents, or any range therein, more preferably in an amount in the range of from about 1.25 to about 1.5 equivalents; in an organic solvent such as THF, toluene, acetonitrile, and the like, preferably, THF; to yield the corresponding compound of formula (Xa). Preferably, the compound of formula (Xa) is not isolated.

The compound of formula (Xa) is reacted with a suitably selected acid, such as HCl, as shown above, according to known methods, to yield the corresponding acid addition salt of the compound of formula (Xa). The compound of formula (Xa) and/or the corresponding acid addition salt of the compound of formula (Xa) may be further, optionally isolated and/or purified according to known methods such as filtration, solvent evaporation, distillation, column chromatography, recrystallization, and the like.

The present invention is further directed to a process for the preparation of the compound of formula (XI), as outline in more detail in Scheme 5 below.

Scheme 5

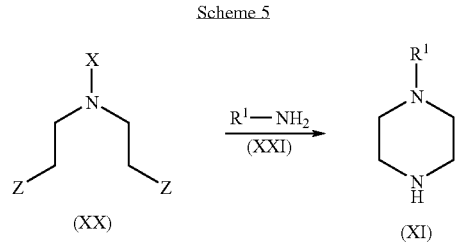

Accordingly, a suitably substituted compound of formula (XX), wherein X is hydrogen or a suitably selected nitrogen protecting group such as —C(O)—CF$_3$, acetyl, benzoyl, BOC, Cbz, and the like, preferably, X is hydrogen or —C(O)—CF$_3$; and wherein Z is selected from suitable leaving groups such as -OMs, —O—SO$_2$—OH, -OTf, -OTs, and the like, and wherein both Z substituents are the same, preferably each Z is -OMs, a known compound or compound prepared according to known methods; is reacted with a compound of formula (XXI), a known compound or compound prepared by known methods; wherein the compound of formula (XXI) is preferably present in an amount in the range of from about 1 to about 2 molar equivalents; or any range therein, in an organic solvent such as THF, toluene, DMF, 2-methyl-THF, acetonitrile, and the like, preferably THF; to yield the corresponding compound of formula (XI).

Alternatively, when X is hydrogen, the compound of formula (XX) is reacted with the compound of formula (XXI) as its corresponding acid additional salt, preferably as its corresponding mono-sulfate salt. Accordingly, the acid addition salt of the compound of formula (XX) wherein X is hydrogen, a known compound or compound prepared by known methods is reacted with a compound of formula (XXI), a known compound or compound prepared by known methods; wherein the compound of formula (XXI) is preferably present in an amount in the range of from about 2 to about 4 molar equivalents, or any range therein, more preferably in an amount in the range of from about 2 to about 3 molar equivalents; in water; to yield the corresponding compound of formula (XI).

The compound of formula (XI) may be further isolated according to known methods, for example by filtration, solvent evaporation, distillations, and the like; and/or optionally further purified according to known methods, for example by column chromatography, recrystallization, and the like.

In an embodiment, the present invention is directed to a process for the preparation of the compound of formula (XIa), as described in more detail in Scheme 6, below.

Scheme 6

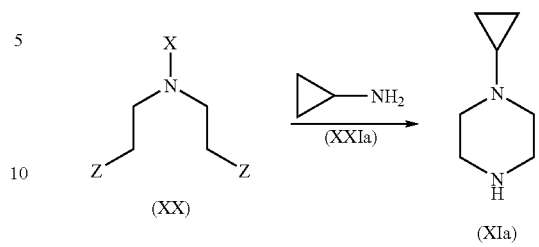

Accordingly, a suitably substituted compound of formula (XX), wherein X is hydrogen or a suitably selected nitrogen protecting group such as —C(O)—CF$_3$, acetyl, benzoyl, BOC, Cbz, and the like, preferably, X is hydrogen or —C(O)—CF$_3$; and wherein Z is selected from suitable leaving groups such as -OMs, —O—SO$_2$—OH, -OTf, -OTs, and the like, and wherein both Z substituents are the same, preferably each Z is -OMs, a known compound or compound prepared according to known methods;
is reacted with a compound of formula (XXIa), also known as cyclopropylamine, a known compound; wherein the compound of formula (XXIa) is preferably present in an amount in the range of from about 1 to about 2 molar equivalents; in an organic solvent such as THF, toluene, DMF, 2-methyl-THF, acetonitrile, and the like, preferably THF; to yield the corresponding compound of formula (XIa).

Alternatively, when X is hydrogen, the compound of formula (XX) is reacted with the compound of formula (XXIa) as its corresponding acid additional salt, preferably as its corresponding mono-sulfate salt. Accordingly, the acid addition salt of the compound of formula (XX) wherein X is hydrogen, a known compound or compound prepared by known methods is reacted with a compound of formula (XXIa), also known as cyclopropylamine, a known compound, wherein the compound of formula (XXIa) is preferably present in an amount in the range of from about 2 to about 4 molar equivalents, more preferably in an amount in the range of from about 2 to about 3 molar equivalents; in water; to yield the corresponding compound of formula (XIa).

The compound of formula (XIa) may be further isolated according to known methods, for example by filtration, solvent evaporation, distillations, and the like; and/or optionally further purified according to known methods, for example by column chromatography, recrystallization, and the like. Preferably, the compound of formula (XIa) is isolated by distillation.

In an embodiment, the present invention is directed to a process for the preparation of the compound of formula (XIb), as described in more detail in Scheme 7, below.

Scheme 7

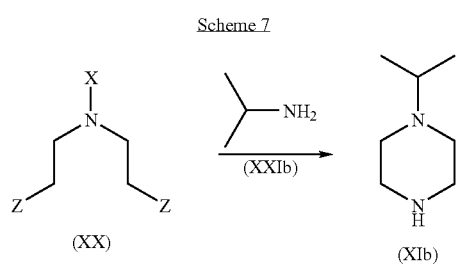

Accordingly, a suitably substituted compound of formula (XX), wherein X is hydrogen or a suitably selected nitrogen protecting group such as —C(O)—CF$_3$, acetyl, benzoyl, BOC, Cbz, and the like, preferably, X is hydrogen or —C(O)—CF$_3$; and wherein Z is selected from suitable leaving groups such as -OMs, —O—SO$_2$—OH, -OTf, -OTs, and the like, and wherein both Z substituents are the same, preferably each Z is -OMs, a known compound or compound prepared according to known methods;

is reacted with a compound of formula (XXIb), also known as isopropylamine, a known compound; wherein the compound of formula (XXIb) is preferably present in an amount in the range of from about 1 to about 2 molar equivalents; in an organic solvent such as THF, toluene, DMF, 2-methyl-THF, acetonitrile, and the like, preferably THF; to yield the corresponding compound of formula (XIb).

Alternatively, when X is hydrogen, the compound of formula (XX) is reacted with the compound of formula (XXIb) as its corresponding acid additional salt, preferably as its corresponding mono-sulfate salt. Accordingly, the acid addition salt of the compound of formula (XX) wherein X is hydrogen, a known compound or compound prepared by known methods is reacted with a compound of formula (XXbI), also known as isopropylamine, a known compound; wherein the compound of formula (XXI) is preferably present in an amount in the range of from about 2 to about 4 molar equivalents, more preferably in an amount in the range of from about 2 to about 3 molar equivalents; in water; to yield the corresponding compound of formula (XI).

The compound of formula (XIb) may be further isolated according to known methods, for example by filtration, solvent evaporation, distillations, and the like; and/or optionally further purified according to known methods, for example by column chromatography, recrystallization, and the like.

One skilled in the art will recognize that in the reactions as described in Schemes 5, 6 and 7 above, the compounds of formula (XXI), (XXIa) or (XXIb), respectively, are acting as both a reagent and as a base. The compounds of formula (XXI), (XXIa) or (XXIb), respectively, and where appropriate, may also act as a solvent.

One skilled in the art will further recognize that the reaction of the compound of formula (XX) with the compound of formula (XXI) may alternatively be carried out in the presence of an additional, tertiary organic or inorganic base such as TEA, DIPEA, pyridine, potassium carbonate, cesium carbonate, sodium bicarbonate, sodium hydroxide, potassium hydroxide, and the like, and the use of said additional base permits the use of a smaller molar amount of the compound of formula (XXI), than in the case where no additional base is added. For example, wherein 1 molar equivalent of the additional tertiary organic or inorganic base is used, then about 1 molar equivalent less of the compound of formula (XXI) is needed.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders and conditions mediated by a histamine receptor described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders or conditions mediated by a histamine receptor is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue"

does not limit the physical state in which the product was isolated and may include, for example, a solid, an oil, a foam, a gum, a syrup, and the like.

EXAMPLE 1

4-Morpholin-4-ylmethyl-benzoic acid methyl ester

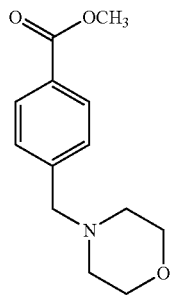

A 2 L, three-neck flask fitted with a mechanical stirrer, addition funnel, and thermocouple probe was charged with 4-formyl-benzoic acid methyl ester (50.0 g, 0.31 mol, 1.0 eq) and 1,2-dichloroethane (700 mL). The resulting mixture was cooled to 10° C. Morpholine (53 mL, 0.61 mol, 2.0 eq) was then added dropwise over 10 min. After 5 min, sodium triacetoxyborohydride (90 g, 0.43 mol, 1.4 eq) was added in portions over 5 min. After stirring 30 min, the reaction mixture was warmed to room temperature. At this point, a slow and steady temperature increase was observed, and a water bath was used to keep the temperature of the reaction mixture below 25° C. The reaction mixture was stirred for 22 hrs at room temperature. Water/ice (100 mL) was added to the reaction and the reaction mixture was stirred for 15 min. NaOH solution (1.0 M in water, 400 mL) was added in several portions, followed by the addition of water (250 mL). The resulting mixture was stirred for 45 min. The layers were separated, and the aqueous layer was extracted with dichloromethane (150 mL). The combined organic layer was washed with brine (150 mL) and then dried over $Na_2SO_4$. The solvent was removed in vacuo to yield the title compound as a pale yellow, viscous oil.

$^1$H-NMR (400 MHz, $CDCl_3$): δ 7.99 (d, 2H, J=8.3 Hz), 7.41 (d, 2H, J=8.5 Hz), 3.91 (s, 3H), 3.72-3.70 (m, 4H), 3.54 (s, 2H), 2.46-2.43 (m, 4H)

$^{13}$C-NMR (126 MHz, $CDCl_3$): δ 167.0, 143.4, 129.6, 129.1, 128.9, 70.0, 63.0, 53.7, 52.0

MS m/z (ESI+): 236.1 (M+H$^+$).

EXAMPLE 2

4-(4-Carboxy-benzyl)-morpholin-4-ium chloride

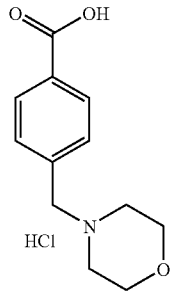

A 200 mL round-bottom flask was charged with 4-morpholin-4-ylmethyl-benzoic acid methyl ester (4.0 g, 0.017 mol, 1.0 eq). A solution of NaOH (2.0 g, 0.051 mol, 3.0 eq) in water was added and the reaction mixture was stirred overnight at room temperature. NaCl (5.0 g) and HCl (6.0 M in water, 17 mL, 6.0 eq) were then added. The reaction mixture was cooled to 0° C. and then stirred for 1 hr. The solid was collected by filtration, washed with pentane and dried at 50° C. under vacuum to yield the title compound as a white solid.

$^1$H-NMR (500 MHz, $d_6$-DMSO): δ 13.1 (br s, 1H), 11.8 (br s, 1H), 7.99 (d, 2H, J=8.1 Hz), 7.79 (d, 2H, J=8.1 Hz), 4.40 (s, 2H), 3.92-3.83 (m, 4H), 3.20-3.10 (m, 4H)

$^{13}$C-NMR (126 MHz, $d_6$-DMSO): 6167.3, 134.5, 132.2, 132.1, 130.0, 63.4, 58.8, 51.2

MS m/z (ESI+): 222.1 (M+H$^+$).

EXAMPLE 3

(4-Cyclopropyl-piperazin-1-yl)-(4-morpholin-4-ylmethyl-phenyl)-methanone

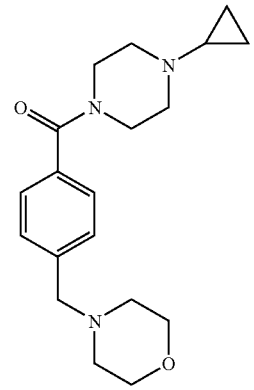

STEP A: A 200 mL round-bottom flask fitted with a reflux condenser was charged with 4-(4-carboxy-benzyl)-morpholin-4-ium chloride (10.0 g, 0.039 mol, 1.0 eq), toluene (50 mL), DMF (0.3 mL, 0.0039 mol, 0.1 eq), and thionyl chloride (7.1 mL, 0.097 mol, 2.5 eq) under a nitrogen atmosphere. The reaction mixture was heated to 70° C. for 6 h and then cooled to 0° C. The resulting mixture was filtered and the solid washed with pentane to yield 4-morpholin-4-ylmethyl-benzoyl chloride, which was used in the next step without further purification.

STEP B: A 250 mL, two-neck flask fitted with an addition funnel and thermocouple probe was charged with 1-cyclopropyl-piperazine dihydrochloride (7.1 g, 0.036 mol, 1.0 eq) and toluene (70 mL) and then cooled to 0° C. Aqueous NaOH solution (1.0 M, 70 mL, 2.0 eq) was added at such a rate that the reaction temperature did not exceed 10° C. $Na_2CO_3$ powder (7.5 g, 0.071 mol, 2.0 eq) was then added to the reaction mixture. The 4-morpholin-4-ylmethyl-benzoyl chloride, prepared as in Step A above (9.8 g, 0.036 mol, 1.0 eq) was added in portions over 3 minutes, while the temperature of the reaction mixture was maintained below 5° C. The reaction mixture was then stirred for 2 hrs. The reaction mixture was filtered, the layers were separated, the aqueous layer was extracted with toluene (30 mL×2), and the combined organic layers washed with brine (30 mL) and dried over $Na_2SO_4$. The solvent was removed in vacuo to yield the title compound as a as pale yellow viscous oil.

$^1$H-NMR (400 MHz, $CDCl_3$): δ 7.35 (br s, 4H), 3.73 (br s, 2H), 3.69 (t, 4H, J=4.6 Hz), 3.50 (s, 2H), 3.37 (br s, 2H), 2.67 (br s, 2H), 2.53 (br s, 2H), 2.43 (t, 4H, J=4.2 Hz), 1.63 (ddd, 1H, J=10.3, 6.7, 3.7 Hz), 0.49-0.43 (m, 2H), 0.42-0.39 (br s, 2H)

13C-NMR (101 MHz, CDCl₃): δ 170.6, 140.0, 135.1, 129.5, 127.5, 67.4, 63.4, 54.0, 38.7, 6.3
MS m/z (ESI+): 330.2 (M+H⁺).

EXAMPLE 4

(4-Cyclopropyl-piperazin-1-yl)-(4-morpholin-4-ylmethyl-phenyl)-methanone dihydrochloride salt

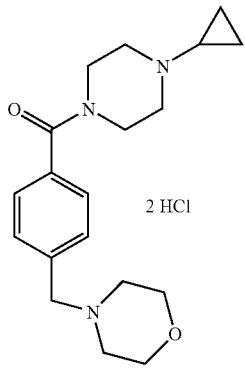

A 250 mL, three-neck flask fitted with a mechanical stirrer, addition funnel, thermocouple probe, and heating mantle was charged with (4-cyclopropyl-piperazin-1-yl)-(4-morpholin-4-ylmethyl-phenyl)-methanone (11.0 g, 0.034 mol, 1.0 eq) and ethanol (75 mL). The resulting solution was heated to 60° C. Concentrated hydrochloric acid (6.1 mL, 0.074 mol, 2.2 eq) was then added dropwise over 8 min. The reaction mixture was then heated at 60° C. for a further 10 min and then slowly cooled to 20° C. over 3 hrs. The resulting solid was collected by filtration, rinsed with pentane, and dried at 50° C. for 3 hrs in a vacuum oven to yield the title compound as a white solid.

¹H-NMR (400 MHz, D₂O): δ 7.64 (pseudo d, J=8.3 Hz, 2H), 7.58 (pseudo d, J=8.3 Hz, 2H), 4.44 (br s, 2H), 4.20-3.10 (m, 16H), 2.88 (ddd, 1H, J=11.2, 6.6, 4.8 Hz), 1.03-0.98 (m, 4H)

¹³C-NMR (101 MHz, D₂O): δ 172.1, 135.3, 132.2, 130.9, 128.0, 64.0, 60.5, 52.6, 52.4, 51.7, 44.8, 39.7, 39.5, 3.9
MS m/z (ESI+): 330.0 (M+H⁺).

EXAMPLE 6

(4-Cyclopropyl-piperazin-1-yl)-(4-morpholin-4-ylmethyl-phenyl)-methanone bis-hydrochloride salt

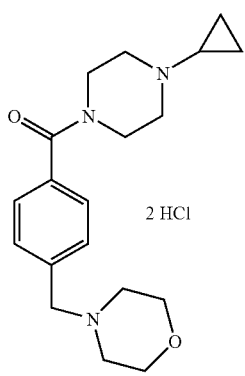

Step A: Preparation

A 100-L glass-lined reactor was charged with toluene (45.00 kg) and stirred at ~20-25° C. To the stirring toluene was added 4-(4-morpholinylmethyl)benzoic acid hydrochloride (6.50 kg, 93.5%, 24.04 mol), 1-hydroxybenzotriazole monohydrate (2.32 kg, 15.13 mol), 1-cyclopropylpiperazine (3.50 kg, 27.07 mol) and acetonitrile (9.00 kg). The resulting off-white slurry was stirred under N₂ at ~20-25° C. for 40 minutes. N-(3-Dimethylaminopropyl)-N'-ethylcarbodiimide hydrochloride (3.50 kg, 27.07 mol) was added, followed by an acetonitrile (1.20 kg) rinse. After the addition, the reaction mixture was stirred at ~20-25° C. overnight. Water (32.50 kg) and aqueous saturated sodium carbonate (19.50 L) were then added to the stirring suspension. The suspension was stirred for an additional 30 minutes. The resulting biphasic solution was allowed to settle. The aqueous phase was discarded and the organic phase was washed with a 50% brine solution [water (19.50 L)/brine (19.50 L)]. To the stirred organic phase was then added anhydrous sodium sulfate (2.86 kg) and the resulting mixture was stirred at ~20-25° C. for 1.5 hours. The solid sodium sulfate was filtered off and the filter cake was washed with acetonitrile (15.30 kg). The filtrate was transferred to a clean 100-L glass-lined reactor and stirred at ~20-25° C. Water (0.47 kg) and 5/6N HCl in 2-propanol were added to precipitate the title compound as the corresponding bis-hydrochloride salt as a solid. The solid was filtered, washed with acetonitrile (10.2 kg) and dried (60 Torr, ~40-45° C.) to a constant weight to yield the title compound as a white solid.

Step B: Purification

In a 50-L glass reactor, the white solid prepared as in Step A above (15.0 kg, 37.28 mol) was dissolved in 1:1 (v/v) mixture of ethanol:water (15.0 L:15.0 L) at ~20-25° C. The resulting mixture was stirred for 45 minutes and polish filtered (to remove any foreign particles) into a clean 100-L glass-lined reactor. The filtrate was transferred to a clean reaction vessel. Upon stirring, (polish filtered) ethanol (75.0 L) was added and the title compound precipitated as a bis-HCL mono-hydrate salt. The resultant white slurry was stirred at ~20-25° C. overnight. The solid was filtered, washed with ethanol (7.5 L) and dried at ~20-25° C. under vacuum to yield the title compound as a monohydrate bis-hydrochloride salt as a white solid.

Karl Fisher analysis showed 3.4-3.6% water present.
Chromatographic Purity (% w/w) showed 96.6%

EXAMPLE 7

Trifluoro-N,N-bis-(2-hydroxy-ethyl)-acetamide

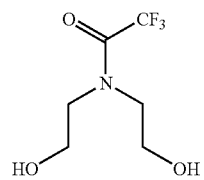

Methyltrifluoroacetate (25 g, 195.3 mmol) was added drop wise to an ice cooled stirred solution of 2,2'-iminodiethanol (20.5 g, 195 mmol) in anhydrous THF (100 mL). The reaction mixture was allowed to warm to ambient temperature naturally and stirred over night at ambient temperature. The solvent was evaporated via rotary evaporation to yield the title compound as a clear oil.

¹H NMR (300 MHz, DMSO-d₆): 3.65 (t, J=5.4 Hz, 4H), 2.95 ((t, J=5.4 Hz, 4H). MS (ESI⁺) m/z 202.14 (MH⁺).

EXAMPLE 8

Methanesulfonic acid 2-[(2-methanesulfonyloxy-ethyl)-(2,2,2-trifluoro-acetyl)-amino]-ethyl ester

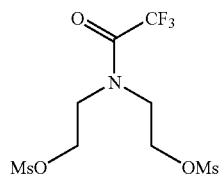

Trifluoro-N,N-bis-(2-hydroxy-ethyl)-acetamide (2.01 g, 10 mmol) of in THF (12 mL) was cooled to ice bath temperature. Triethylamine (20.1 mol, 2.3 g=1.56 mol) was added between 5-10° C. Methanesulphonyl chloride was then added to the reaction mixture at a temperature between 5-10° C. The reaction mixture was stirred for 1 h at 5-10° C. and then allowed to warm to ambient temperature overnight. The resulting precipitated solids were filtered off and the reaction flask was rinsed with THF (2×10 mL portions), then filtered. The filtrate was concentrated to yield the title compound as a clear thick oil.

¹H NMR (400 MHz, CDCl₃): (m, 4.67-4.38, 4H), 3.91-3.84 (m, 4H), 3.07 (s, 3H), 3.05 (s, 3H).

EXAMPLE 9

1-(4-Cyclopropyl-piperazin-1-yl)-2,2,2-trifluoro-ethanone

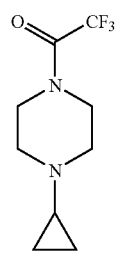

The product prepared as in Example 8 above, methanesulfonic acid 2-[(2-methanesulfonyloxy-ethyl)-(2,2,2-trifluoro-acetyl)-amino]-ethyl ester (3.6 g) was dissolved in THF (18 mL). Cyclopropylamine (1.14 g, 20 mmol) was then added neat to the reaction mixture. The reaction mixture was then heated at 48° C. for 72 hours. The reaction mixture was then concentrated to a thick oil and the oil was chromatographed using 25-35% ethylacetate-hexanes mixture to yield the title compound as the late eluting fraction and isolated as thick brown oil.

¹H NMR (300 MHz, CDCl₃): 3.70-3.54 (2 m, 4H), 2.68-2.65 (m, 4H), 1.69-1.63 (m, 1H), 0.53-0.34 (2 m, 4H)

EXAMPLE 10

1-Cyclopropylpiperazine dihydrochloride

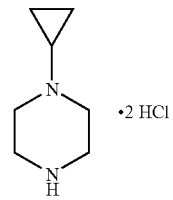

To 1-(4-cyclopropyl-piperazin-1-yl)-2,2,2-trifluoro-ethanone (444.4 mg, 2 mmol) was added a mixture of HCl/IPA (5-6N, 2 mL). Solids were observed to precipitate immediately after the HCl/IPA was added. The resulting suspension was stirred for 5 h. Heptane (2 mL) was then added to the reaction mixture, followed by addition of IPA (2 mL). The resulting suspension was stirred for 0.5 h at ambient temperature. The solids were filtered off using a medium glass sintered funnel with a filter paper on the top. The reaction flask was rinsed with IPA (3 mL) and the rinse was used to wash the solids. The solid was washed a second time with fresh IPA (2 mL). The solids were dried at ambient temperature and house vacuum to yield the title compound as a white crystalline solid.

¹H NMR (300 MHz, D₂O): 3.67-3.29 (2 m, 8H), 2.80-2.75 (m, 1H), 0.91-0.89 (m, 4H).

EXAMPLE 11

Sulfuric acid mono-[2-(2-sulfooxy-ethylamino)-ethyl]ester

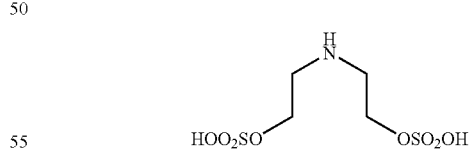

Diethanolamine (10.84 g) was heated with concentrated H₂SO₄ (20.13 g) at about 10-15 mm vacuum (house vacuum) and at a temperature in the range of about 175-180° C. for 5.5 h. The resulting solution was cooled to ambient temperature and stirred over the weekend under nitrogen. The resulting light brown solution was determined by ¹H NMR to contain the title compound in solution.

¹H NMR (300 MHz, DMSO-d₆): δ 4.5 (bs, 1H), 3.43, (t, J=6 Hz, 4H), 2.56 (t, J=6 Hz, 4H).

EXAMPLE 12

1-Cyclopropylpiperazine

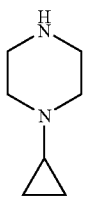

A carousel tube was charged with sulfuric acid mono-[2-(2-sulfooxy-ethylamino)-ethyl]ester (1 g) and D$_2$O (3 mL). To the resulting stirred solution was added then added cyclopropylamin (0.7 mL). The resulting mixture was observed to form a stirrable thick slurry, which was heated at 50° C. overnight. Comparison of the 1H NMR of the title compound with the 1H NMR of the di-hydrochloride salt of the title compound confirmed that the title compound was prepared and present in the resulting solution.

MS (ESI$^+$) m/z 127.2 (MH$^+$), 275.1 (2MW+Na).

EXAMPLE 13

(4-Isopropyl-piperazin-1-yl)-(4-morpholin-4-ylmethyl-phenyl)-methanone succinate salt

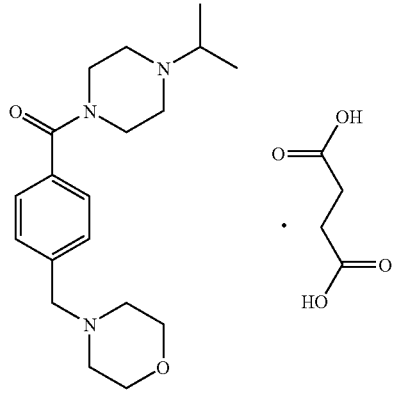

Step A: Free Base Preparation

A 1 L three-necked flask equipped with an air stirrer and thermocouple was charged with 4-(4-morpholinylmethyl) benzoic acid hydrochloride (50 g, 0.194 mol), toluene (400 mL), acetonitrile (100 mL) and 1-hydroxybenzotriazole monohydrate (17.8 g, 0.116 mol). After stirring the resulting off-white slurry at about 20-25° C. for 5 minutes, 1-isopropyl-piperazine (27.4 g, 0.213 mol) was added and the reaction mixture was stirred for 20 minutes. Next, N-(3-dimethylaminopropyl)-N'-ethylcarbodiimide hydrochloride (44.6 g, 0.233 mol) was added and the reaction mixture was stirred at about 20-25° C. overnight. Water (250 mL) and aqueous saturated sodium carbonate (150 mL) were then added to the stirring suspension and mixed well. The resulting biphasic mixture was allowed to settle. The aqueous phase was discarded and the organic phase was washed with a 50% brine solution (water (150 mL)/brine (150 mL)). The organic phase was dried over anhydrous sodium sulfate, filtered, washed with acetonitrile and concentrated to yield (4-isopropyl-piperazin-1-yl)-(4-morpholin-4-ylmethyl-phenyl)-methanone, as a free base, as a light yellow oil.

Step B: Preparation or Succinate Salt

The free base prepared as in Step A above (56.2 g, 0.17 mol) was dissolved in ethanol (562 mL). The resulting mixture was heated to about 60-65° C. Succinic acid was then added to the reaction mixture. Upon cooling to room temperature, a solid was observed to precipitate. The suspension was stirred for 30 minutes, then cooled to about 0-10° C. and stirred for an additional 30 minutes. The suspension was filtered, the solid collected and dried, to yield the title compound.

The presence of the title compound was confirmed by HPLC analysis.

EXAMPLE 14

(4-Isopropyl-piperazin-1-yl)-(4-morpholin-4-ylmethyl-phenyl)-methanone)-bishydrochloride-monohydrate

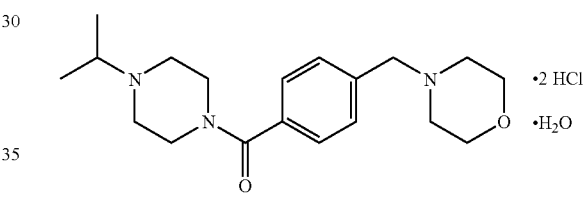

To an 18 L reactor, equipped with an overhead stirrer, condenser with nitrogen inlet, addition funnel and a thermocouple at 20° C. was added (4-Isopropyl-piperazin-1-yl)-(4-morpholin-4-ylmethyl-phenyl)-methanone) succinate (976.4 g, 2.18 mol), 2-methyl-tetrahydrofuryl (10.8 L) and the resulting suspension was stirred. To the resulting mixture, over about 10 minutes) was then added 45% aqueous KOH (597 mL, 4.80 mol) via a liquid dropping funnel and the suspension stirred to complete dissolution. To the resulting mixture was added water (0.5 L) to dissolve the turbid bottom layer. The phases were allowed to separate and then the bottom, aqueous layer was discarded. To the top organic layer was added additional water (3.8 L) and the resulting mixture stirred for 0.5 h. The layers were allowed to separate and the bottom aqueous layer was discarded. The organic layer was dried with anhydrous Na$_2$SO$_4$ (500 g), stirring for 15 minutes. The organic layer was filtered to remove the solid.

To the filtered organic layer, over about 15 minutes, while maintaining the reactor at 20° C., was added a mixture of 5/6N HCl/IPA (765 mL, 3.90 mol). A solid was observed to precipitate. The resulting mixture was stirred at 20° C. for 3.5 hours. The solids were filtered via a Büchner funnel covered with a Dacron cloth. The reactor was rinsed with 2-methyl-tetrahydrofuran (0.5 L) and the rinse used to wash the filtered solids. The filter cake was washed with additional 2-methyl-tetrahyrofuran (0.5 L). The filter cake was allowed to air dry for 1 h, then dried at 30° C. under vacuum (28 mm/Hg) until constant weight to yield the title compound as white crystalline solid.

Analytical Analysis: C, 54.05%; H, 8.32%; N, 9.86%; Cl⁻, 16.65%;

Karl-Fischer: 4.82%

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (Ia)

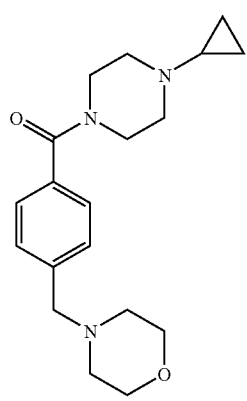

or a pharmaceutically acceptable salt, ester, tautomer or amides thereof; wherein comprising

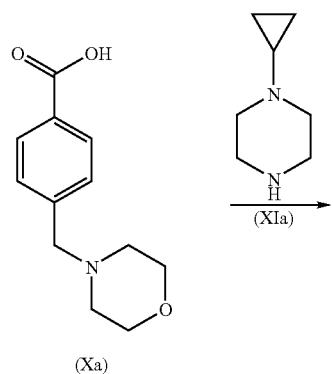

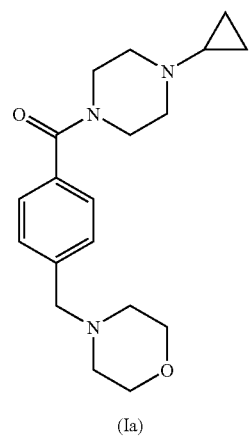

reacting a compound of formula (Xa) with a compound of formula (XIa); in an organic solvent or mixture of organic solvents; to yield the corresponding compound of formula (Ia).

2. A process for the preparation of a compound of formula (Ia)

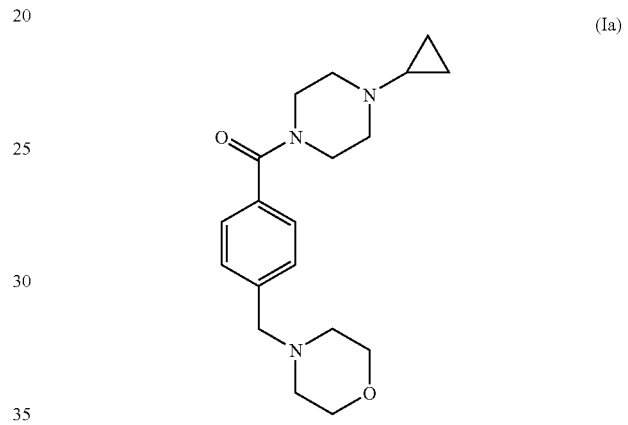

or a pharmaceutically acceptable salt, ester, tautomer, or amide thereof; wherein comprising

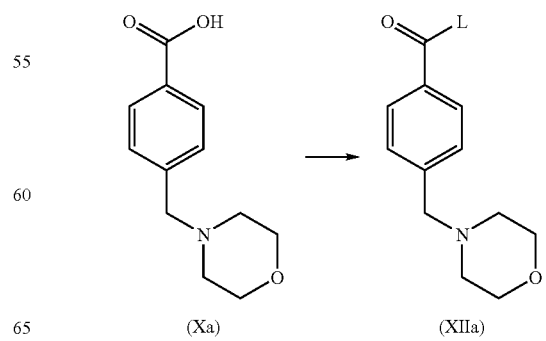

activating a compound of formula (Xa), to yield the corresponding compound of formula (XIIa), wherein L is a leaving group;
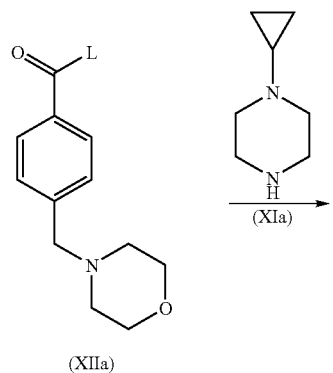
(XIIa)
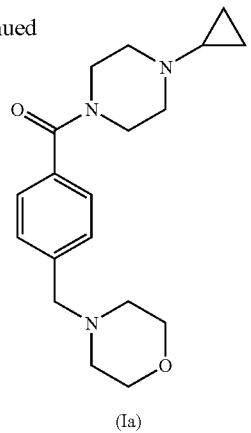
(Ia)
reacting the compound of formula (XIIa) with a compound of formula (XIa); in a solvent or mixture of solvents; to yield the corresponding compound of formula (Ia).
* * * * *